United States Patent [19]

Anderson

[11] Plant 4,501

[45] Feb. 12, 1980

[54] PLUM TREE

[75] Inventor: Frederic W. Anderson, Merced, Calif.

[73] Assignee: Reedley Nursery, Inc., Reedley, Calif.

[21] Appl. No.: 2,784

[22] Filed: Jan. 11, 1979

[51] Int. Cl.[2] ..... A01H 5/03

[52] U.S. Cl. ..... Plt./38

[58] Field of Search ..... Plt./38

*Primary Examiner*—Robert E. Bagwill

*Assistant Examiner*—James R. Feyrer

*Attorney, Agent, or Firm*—Roger B. Webster

[57] ABSTRACT

A plum tree which is of medium size, vigorous, spreading, and open; foliated with medium size, obovate, medium thick, smooth leaves having a crenate margin and alternate, globose glands; bears short, obtuse flower buds which bloom white; and is a regular and very productive bearer of large to medium size, uniform, globose to oblong, cordate, late-ripening, freestone fruit having yellow skin substantially overspread with red, yellow flesh, and a small stone.

1 Drawing Figure

BACKGROUND OF THE VARIETY

1. Field of the Invention

Over a substantial number of years I have engaged in an extensive and continuing plant breeding program at my experimental nursery and orchard located near Le Grand, Merced County, Calif.; one purpose of such program being to provide improved varieties of fruit trees. The present variety of plum tree resulted from my endeavors in the conduct of such plant breeding program; such variety being embraced by Class 38, Plants, of the U.S. Patent Office Manual of Classification.

2. Prior Varieties

Among the existent varieties of plum trees which are known to me, I make particular reference to the Ebony (U.S. Plant Pat. No. 2,049) and the Cassellman (unpatented)—both mentioned hereinafter in this specification.

ORIGIN OF THE VARIETY

The present variety of plum tree was originated by me, in my experimental nursery and orchard located as aforesaid, as a seedling of the Ebony plum. More particularly, a large number of seedlings of the Ebony plum were grown under conditions of careful and continuing observation, and when one of such seedlings (and which is the present variety) evidenced new and distinct, and commercially desirable, characteristics, I selected it for asexual reproduction.

ASEXUAL REPRODUCTION OF THE VARIETY

Subsequent to origination and selection by me of the present variety of plum tree, I asexually reproduced it by top-working on mature plum trees in my said experimental orchard, and—in maturity—such reproductions ran true to the original tree in all respects.

SUMMARY OF THE VARIETY

The herein-claimed new and distinct variety of plum tree is of medium size, vigorous, spreading, and open; foliated with medium size, obovate, medium thick, smooth leaves having a crenate margin and alternate, globose glands; bears short, obtuse flower buds which bloom white; and is a regular and very productive bearer of large to medium size, uniform, globose to oblong, cordate, late-ripening, freestone fruit having yellow skin substantially overspread with red, yellow flesh, and a small stone.

The variety is further characterized, in comparison to the Cassellman, by late ripening freestone fruit having less red exterior color at harvest, but which red color intensifies during shipment and storage.

BRIEF DESCRIPTION OF THE DRAWING

The drawing is an illustration, by photographic reproduction in color, of a twig with leaves, and separate fruit; one of the latter being cut into halves, with the stone remaining in one half.

DESCRIPTION OF THE VARIETY

The botanical details of this new and distinct variety of plum tree—with color definitions (except those in common color terms) referenced to Maerz and Paul Dictionary of Color—are as follows:

Tree:
- *Size.*—Medium.
- *Vigor.*—Vigorous.
- *Growth.*—Spreading.
- *Density.*—Open.
- *Production.*—Very productive.
- *Bearing.*—Regular bearer.

Trunk:
- *Size.*—Medium.

Branches:
- *Size.*—Medium.
- *Lenticels.*—Number — medium. Size — medium.

Leaves:
- *Size.*—Medium. Average length — 4". Average width — 1½".
- *Form.*—Obovate.
- *Thickness.*—Medium.
- *Texture.*—Smooth.
- *Margin.*—Crenate.
- *Petiole.*—Medium length. Medium thickness.
- *Glands.*—Number and position — usually 2 on petiole and 2 on blade. Alternate. Medium size. Globose.
- *Color.*—Top side — Medium green (23-L-6). Under side — Lighter green (22-K-7).

Flower buds:
- *Length.*—Short.

*Form.*—Obtuse.

Flowers:

*Blooming period.*—Date of first bloom: Mar. 3, 1978. Date of full bloom: Mar. 12, 1978. Medium, as compared with other varieties.

*Size.*—Medium.

*Color.*—White.

Fruit:

*Maturity when described.*—Hard.

*Date of first picking.*—Sept. 20, 1978.

*Date of last picking.*—Oct. 10, 1978.

*Size.*—Variable. Large to medium. Average diameter axially — 2". Average transversely in suture plane — 1½".

*Form.*—Uniform. Symmetrical. Globose to oblong. Cordate.

*Suture.*—Shallow, with slight depression beyond pistil point.

*Ventral surface.*—Rounded slightly.

*Cavity.*—Rounded.

*Base.*—Rounded.

*Apex.*—Short. Mammiform.

*Pistil point.*—Oblique.

Skin:

*Thickness.*—Medium.

*Tendency to crack.*—Slight to none in wet-dry season.

*Down.*—Wanting.

*Color.*—Yellow (12-K-6) substantially overspread with red (4-L-9) with many yellow flecks.

Flesh:

*Color.*—Yellow (11-L-4).

*Surface of pit cavity.*—Yellow.

*Juice.*—Moderate.

*Texture.*—Firm. Crisp.

*Ripens.*—Evenly.

*Flavor.*—Subacid. Mild. Delicate.

*Aroma.*—Wanting.

*Eating quality.*—Good to best.

Stone:

*Type.*—Free.

*Size.*—Small. Average length — ¾". Average breadth — ⅜". Average thickness — ¼".

*Form.*—Oblong.

*Base.*—Straight.

*Hilum.*—Narrow.

*Apex.*—Rounded.

*Sides.*—Equal.

*Dorsal edge.*—Shallow groove throughout.

*Color.*—Brown (15-E-12).

*Tendency to split.*—Slight in wet season.

Use: Market; dessert; canning; shipping.

Keeping quality: Good.

Resistance to insects and diseases: No unusual susceptibilities noted.

Shipping quality: Good.

The plum tree and its fruit herein described may vary in slight detail due to climatic and soil conditions under which the variety may be grown; the present description being of the variety as grown in the Central Valley of California.

I claim:

1. A new and distinct variety of plum tree, substantially as illustrated and described, characterized, in comparison to the Cassellman, by late ripening freestone fruit having less red exterior color at harvest but which red color intensifies during shipment and storage.

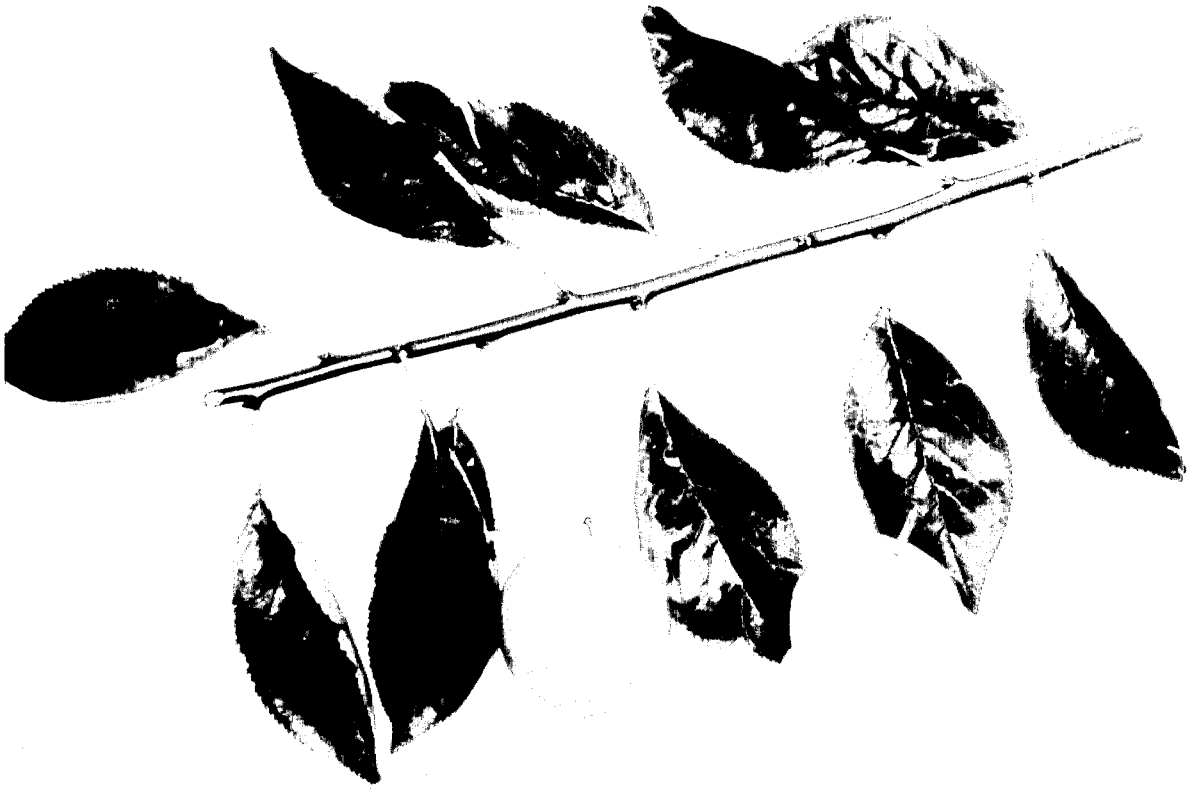

* * * * *